US00PP15650P3

(12) United States Plant Patent
Wolfram

(10) Patent No.: US PP15,650 P3
(45) Date of Patent: Mar. 15, 2005

(54) ***PRUNUS* TREE ROOTSTOCK NAMED 'PIKU 4'**

(50) Latin Name: *Prunus L.*
Varietal Denomination: Piku 4

(75) Inventor: Brigitte Wolfram, Dresden (DE)

(73) Assignee: Bundesanstalt fur Zuchtungstorschung an Kulturpflanzen, Quedlinburg (DE)

( * ) Notice: Subject to any disclaimer, the term of this patent is extended or adjusted under 35 U.S.C. 154(b) by 140 days.

(21) Appl. No.: 10/136,467

(22) Filed: May 1, 2002

(65) Prior Publication Data

US 2003/0208808 P1 Nov. 6, 2003

(51) Int. Cl.[7] ..... A01H 5/00
(52) U.S. Cl. ..... Plt./183
(58) Field of Search ..... Plt./183

*Primary Examiner*—Bruce R. Campell
*Assistant Examiner*—Annette H Para
(74) *Attorney, Agent, or Firm*—Webb Ziesenheim Logsdon Orkin & Hanson, P.C.

(57) ABSTRACT

A new and distinct *Prunus* rootstock compatible with other *Prunus* varieties and producing trees with reduced growth, suitable to sandy soil with high productivity.

3 Drawing Sheets

Classification: *Prunus L.*
Varietal denomination: 'Piku 4'.

BACKGROUND OF THE INVENTION

The present invention comprises a new and distinct cultivar of hybrid *Prunus* known by the varietal name 'Piku 4'. The new variety was discovered in 1976 in a selective breeding program designed to produce growth reducing rootstock for cherry trees in Dresden-Pillnitz, Germany as a cross between an unnamed, unpatented variety of *Prunus cerasus* (Schattenmorelle) (female parent) and an unnamed, unpatented variety of *Prunus* "Kursar" (*P. kurilensis*×*P. sargentii*) (male parent). The new variety differs from its parents in its growth habit. The following characteristic distinguish the new variety from *Prunus avium* rootstock varieties:

1. Three-way hybrid.
2. Reduces growth in grafted varieties by 30–40%.
3. Suitable for sandy soil.
4. Precocious crop.
5. Glossiness of upper leaf surface.
6. Growth habit.

The new variety was first asexually reproduced via green cuttings in 1980 in Dresden-Pillnitz, Germany and subsequent propagation therein has confirmed that the characteristics of the new variety are stable and are transmitted to subsequent generations.

DESCRIPTION OF THE DRAWING

The accompanying photographic drawings illustrate the new variety, with the color being as nearly true as is possible with color illustrations of this type.

DESCRIPTION OF THE PLANT

Figure 1:
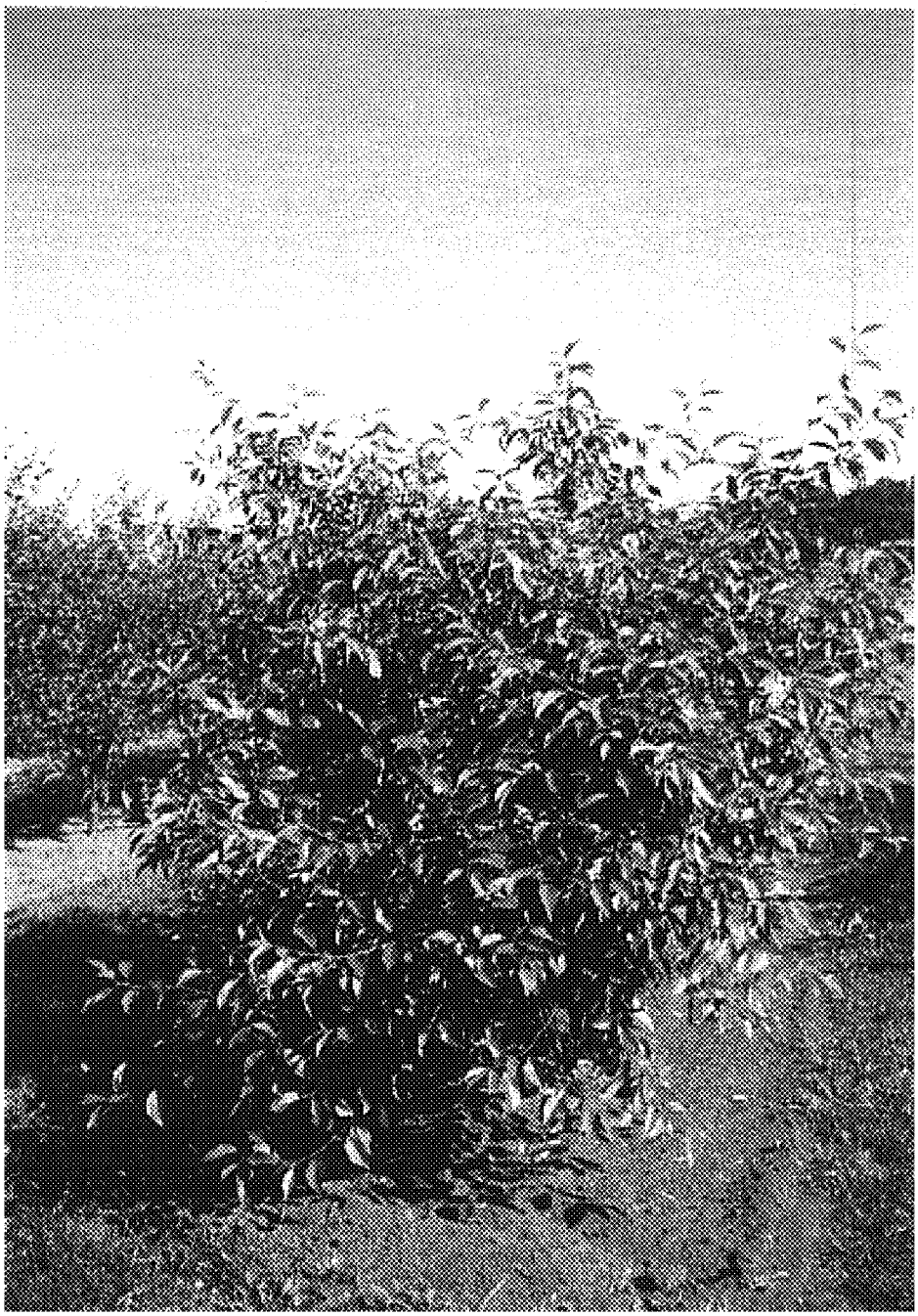
FIG. 1 shows the tree of the new variety.
Figure 2:
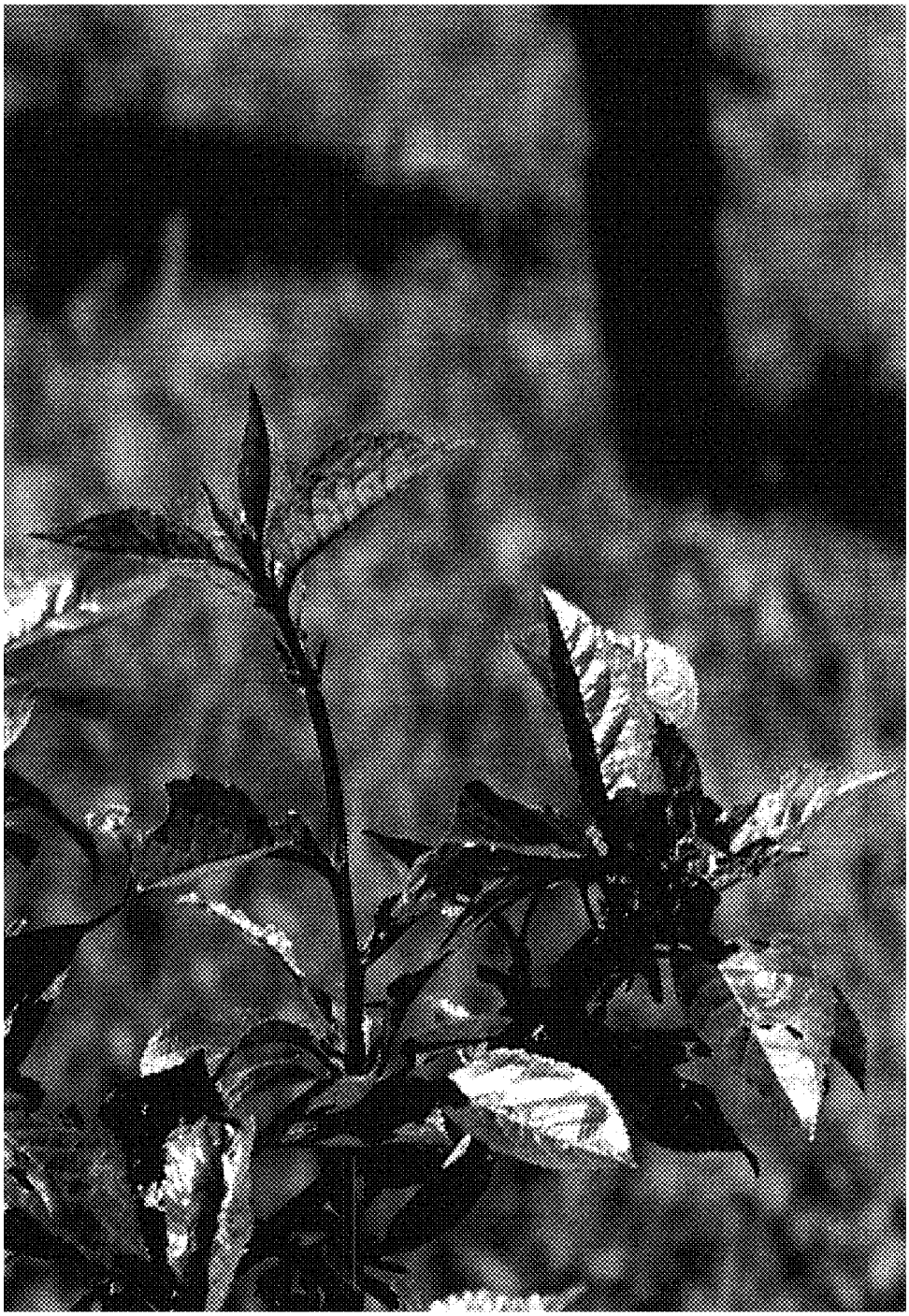
FIG. 2 shows a branch with leaves.
Figure 3:
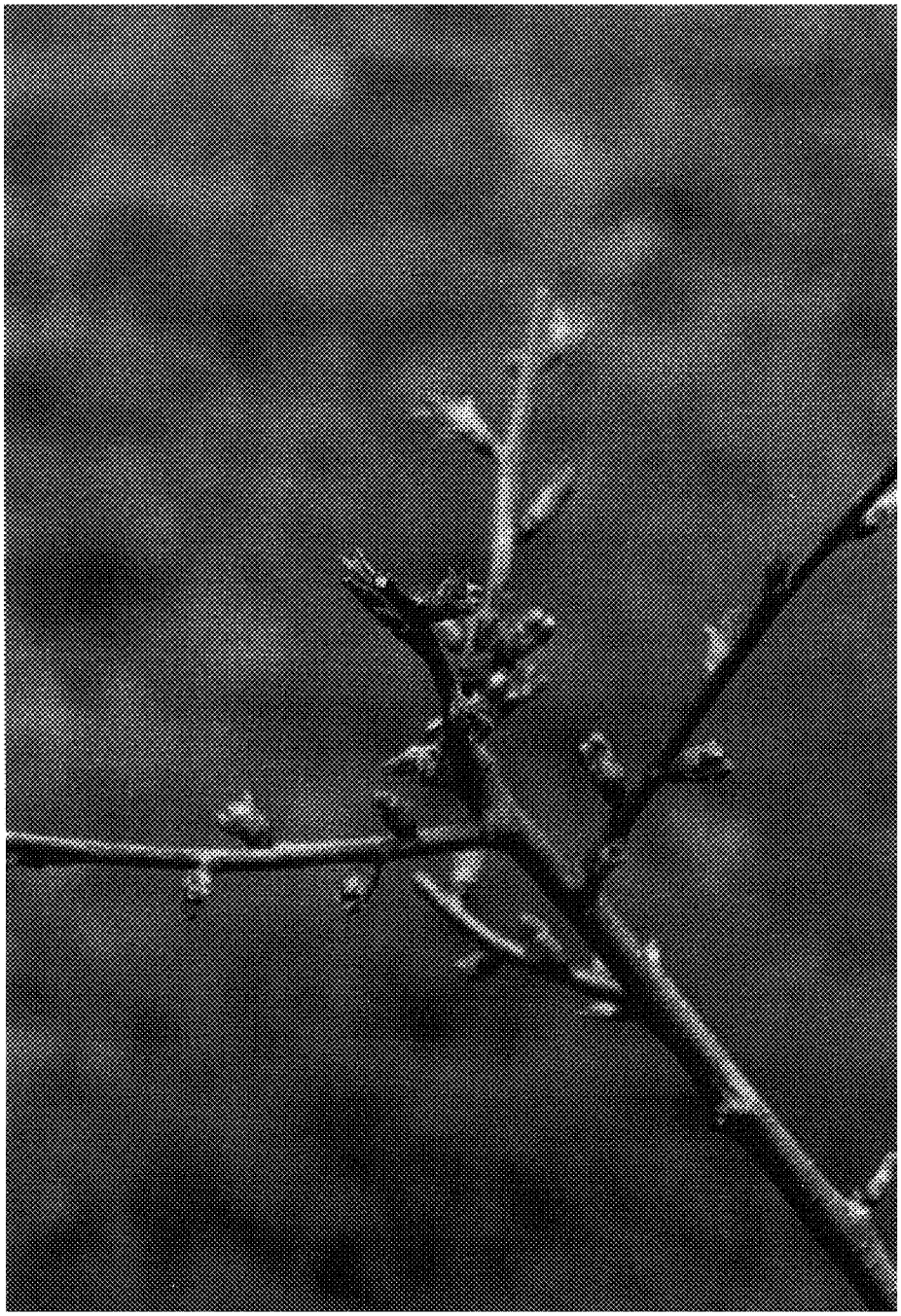
FIG. 3 shows a branch with flower buds.

The following detailed description sets forth the characteristics of the new cultivar. The data which defines these characteristics were collected by asexual reproductions via green cuttings carried out in Dresden-Pillnitz, Germany. The color designations were taken outdoors in Dresden-Pillnitz, Germany. Rootstocks were 6 to 7 years old when described. Color designations are noted with reference to standard *P. avium* rootstock. The new variety prefers dry or sandy soil and is free of PNRV and PDV. As a rootstock, it can be reproduced via softwood cuttings or tissue culture. The new variety anchors adequately with some root sprouts, sufficient compatibility with grafts and exhibits dwarf growth vigor.

TREE

Size: Small-medium; having an average height of 1.90 m and an average width of 2.00 m.
Form: Bushy, drooping.
Trunk:
- *Surface texture.*—Smooth.
- *Bark color.*—Dark.
- *Diameter.*—5.0 cm, measured at a height of 40 cm.

Branches:
- *Surface texture.*—Smooth.
- *Bark color.*—200A.
- *New growth color.*—Light red.
- *Mature growth color.*—Brown.
- *Average crotch angle.*—60–80°.
- *Internode length.*—Medium.
- *Lenticels.*—Diameter: 0.05–0.15 cm. Color: 161A. Amount per shoot: >100.
- *Bud.*—Medium, round.

Leaves:
- *Length.*—10.4 cm.
- *Width.*—5.0 cm.
- *Surface texture.*—Upper side glossy.
- *Form.*—Elongated, elliptical.
- *Color.*—Upper Surface: 146A. Lower Surface: 146B.

Petioles:
- *Length.*—1.7 cm.
- *Thickness.*—0.15 cm.

Leaf glands:
*Quantity.*—1–4.
*Position.*—Under leaf end.
*Size.*—0.20 cm.
*Color.*—Green-red.
Stipules:
*Length.*—1.0–1.2 cm.
Flowers:
*Diameter.*—2.50 cm.
*Color.*—Upper Surface: N155A. Lower Surface: N155A.
*Number.*—Many.
*Petals.*—Length: Approximately 1.2 cm. Width: Approximately 0.8 cm. Quantity per flower: 5.
*Sexual characteristics.*—Triploid, crop is rare.
*Stamen number.*—>10.
*Pistil number.*—1.

FRUIT

Maturity date/location: Mid-season in Dresden, Pillnitz.
Weight: 2 grams.
Axial diameter: 1–2 cm.
Fruit stone:
*Length.*—Approximately 0.6 cm.
*Diameter.*—Approximately 0.5 cm.
Skin: 187A.
Flesh color: 187A.

GENERAL

Weather hardiness: Sufficient tolerance to winter frost.
Disease resistance: Tolerance to Cytospora.

I claim:

1. A new and distinct variety of *Prunus* rootstock named 'Piku 4' substantially as shown and described.

* * * * *